United States Patent [19]

Yamamoto

[11] Patent Number: 4,556,515
[45] Date of Patent: Dec. 3, 1985

[54] MANUFACTURING PROCESS OF β-ACYLENAMINE

[75] Inventor: Hisashi Yamamoto, Nagoya, Japan

[73] Assignee: Toyo Stauffer Chemical Co., Ltd., Tokyo, Japan

[21] Appl. No.: 584,357

[22] Filed: Feb. 28, 1984

[30] Foreign Application Priority Data

Mar. 9, 1983 [JP] Japan ................... 58-38449

[51] Int. Cl.⁴ ................... C07D 237/00; C07D 251/00
[52] U.S. Cl. ................... 260/239 B; 564/453; 564/454; 564/487; 564/502; 549/273
[58] Field of Search ............... 564/453, 454, 487, 502; 260/239 B; 549/273

[56] References Cited

PUBLICATIONS

J.A.C.S. 90:16, Jul. 31, 1968, pp. 4462–4464.
J.A.C.S. 90:16, Jul. 31, 1981, pp. 103, 7368–7370.
J. Am. Chem. Soc., vol. 105, No. 20, 1983, pp. 6312–6314.

Primary Examiner—John Kight
Assistant Examiner—M. L. Moore
Attorney, Agent, or Firm—Armstrong, Nikaido, Marmelstein & Kubovcik

[57] ABSTRACT

A method for preparing β-acylenamine by condensing an oxime sulfonate with silyl enol ether in the presence of reagent, particularly the oxime sulfonate being represented by the following general formula.

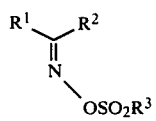

6 Claims, 15 Drawing Figures

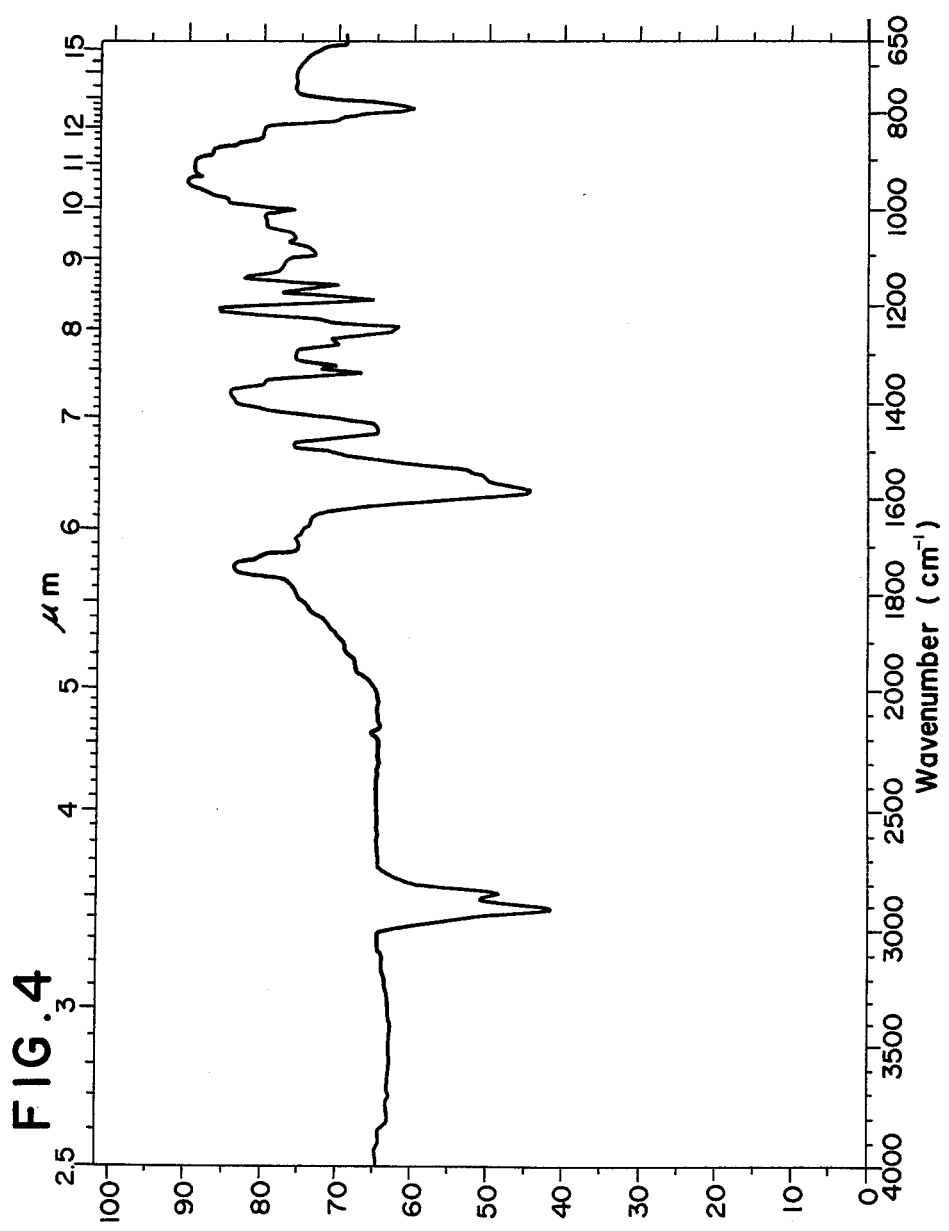

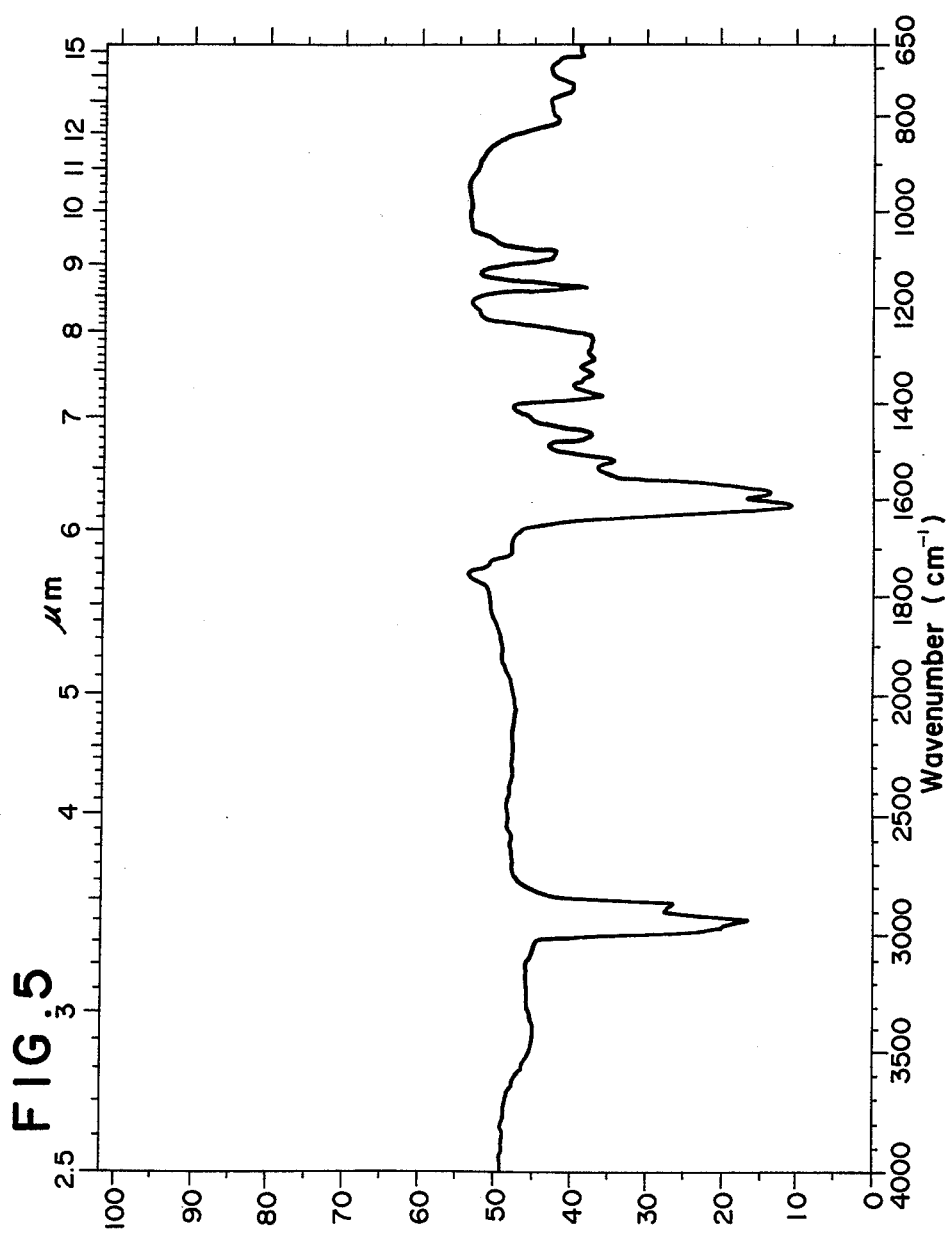

MANUFACTURING PROCESS OF β-ACYLENAMINE

DETAILED DESCRIPTION OF THE INVENTION

The present invention concerns the preparation of β-acylenamine useful for the manufacture of alkaloid. Recently, substances originating from living bodies (hereinafter referred to as natural products) have been vigorously reconsidered in the field of medical supplies and agricultural chemicals.

Among them, there are useful natural products such as alkaloids. Since alkaloids are distributed widely in the plant kingdom and many of them exhibit a remarkable physiological activity, they are used for medical supplies. In order to get alkaloids from the plant, however, a large quantity of living bodies should be gathered for the extraction and the refinement resulting in a high cost of the manufactured alkaloids. For this reason, an attempt has been made to produce alkaloids cheaply in large quantities by chemical methods. For example, there is biosynthesis employing an enzyme. Also, as another method, chemical synthesis is studied in recent years.

Alkaloids are plant bases containing nitrogen, and many of them have a complex structure. A complicated route is necessary for the chemical synthesis. The inventor had attempted to develop a method introducing an alkyl group to the carbon atom of an amine at α-position in order to synthesize the alkaloid chemically through a simpler course and a method of preparing an amine capable of use as an alkaloid intermediate was developed. In this method an oxime sulfonate is first treated with an organoaluminum compound and then reduced with diisobutylaluminum hydride (J. Am. Chem. Soc., Vol. 103, No. 24, P. 7368-7370, 1981). This can be shown by the following equation.

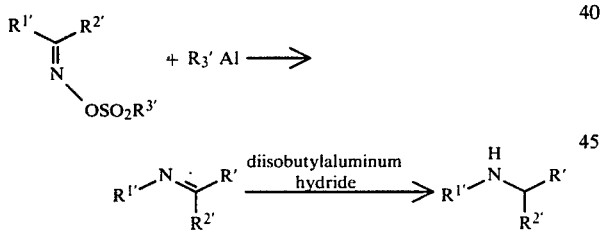

where $R^{1'}$, $R^{2'}$, $R^{3'}$ and $R'$ indicate an alkl group, respectively.

However, in order to introduce an alkyl group having a complex structure by this method, it is necessary to prepare the alkyl group (R) bonded to Al in organoaluminum compounds ($R'_3Al$). Moreover, since close attention should be paid to the handling of organoaluminum compounds because of their flammability and there are also some problems for the synthesis, it is difficult to synthesize organoaluminum compounds having a complex structure.

Accordingly, the alkyl groups capable of being introduced into the intended amine are confined to those having a simple structure and, as a result, there is a restriction that is impossible to manufacture alkaloid intermediates except those having a simple structure.

The inventor has developed the present invention making an effort to determine an alkylating agent and a simpler method to make the alkaloid through the introduction of an alkyl group having more complex structure and synthesizing an intermediate closer to the structure of the alkaloid in one step and yet in high yield.

Namely, the present invention provides a new method of making a β-acylenamine comprising condensing an oxime sulfonate with a silyl enol ether in the presence of a reagent.

β-acylenamine in the invention can be used for the synthesis of, for example, hygrine after being converted to, for example, β-amino ketone through hydrogenation, and the β-amino ketone is used for the synthesis of, for example, sedamine after being converted further to β-amino alcohol through reduction.

According to the invention, β-acylenamine having a specific stereochemistry can also be manufactured by the chemical synthesis in high yield, and the industrial significance of the invention is enormous as can be understood from the embodied explanation described below.

In the invention, the reagents that can be used are compounds of metal belonging to a or b of the first to the fourth group, a of the fifth to the seventh group, or the eighth group of the periodic table, and the use of Al compounds is particularly advantageous. Among these reagents, those represented by the general formula $R_nAlX_{3-n}$ [where R indicates an alkyl group having 1 to 20 carbon atoms, X indicates hydrogen atom, halogen atom, —OR″ (R″ is an alkyl group having 1 to 20 carbon atoms), —CN or

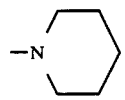

(a substituent may be present at 2- or 6- position) and n is a real number limited by $0 \leq n \leq 3$.] are particularly preferable.

The manufacturing process of β-acylenamine in the invention is shown by the following equation.

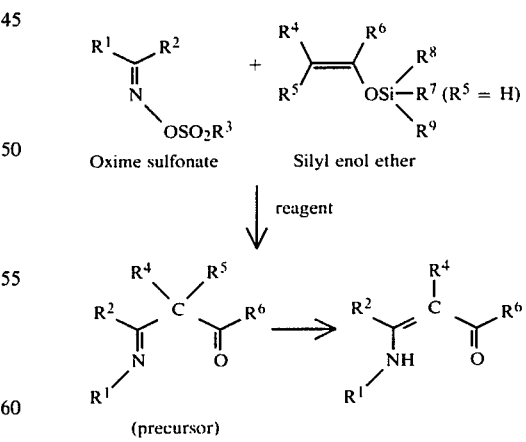

$R^1$, $R^2$, $R^3$, $R^4$, $R^5$, $R^6$, $R^7$, $R^8$ and $R^9$ in the above formulas are defined as follows:

$R^1$, $R^2$: Hydrogen or a straight-chain or branched-chain and saturated or unsaturated aliphatic, cycloaliphatic (alicyclic) or aromatic hydrocarbon group having 1 to 30 carbon atoms and which can contain N, O, P or S and form a ring through the combination of $R^1$ and $R^2$.

$R^3$: A straight-chain or branched-chain and saturated or unsaturated aliphatic, cycloaliphatic (alicyclic) or aromatic hydrocarbon group having 1 to 20 carbon atoms.

$R^4$, $R^5$, $R^6$: Same as $R^1$ and $R^2$, but may form a ring through the combination of $R^4$ and $R^5$ or $R^4$ and $R^6$.

$R^7$, $R^8$, $R^9$: Same as $R^3$.

As evident from this description, the process of the present invention has characteristics which make it possible to manufacture β-acylenamine, which is an intermediate closer to an alkaloid structurally and capable of simplifying the synthesis of an alkaloid, in one step and yet in high yield by a new method comprising condensing an oxime sulfonate with a silyl enol ether without using the organoaluminum compound ($R'_3Al$) having the defects described above.

In the following, the invention will be explained concretely. The oxime sulfonates usable in the invention are compounds represented by the general formula

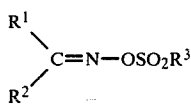

[$R^1$ and $R^2$ are hydrogen or a straight-chain or branched-chain, saturated or unsaturated aliphatic, cycloaliphatic (alicyclic) or aromatic hydrocarbon group having a number of carbon atom 1 to 30 carbon atoms, and which (may contain N, O, P or S) and $R^1$ and $R^2$ may be combined to form a ring. $R^3$ is a straight-chain or branched-chain, saturated or unsaturated aliphatic, cycloaliphatic (alicyclic) or aromatic hydrocarbon group having 1 to 20 carbon atoms.]. The following are examples,

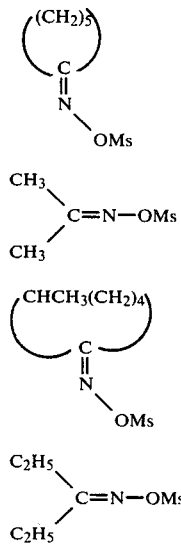

and the like (where Ms and Ts indicate mesyl and tosyl, respectively).

Taking up cyclohexanoneoxime as an example, this compound can be obtained as white crystals having a m.p. of 43 to 45° C. by stirring of cyclohexanoneoxime with methanesulfonyl chloride and triethylamine for about 10 min at −20° C. in methylene chloride and thereafter extracting and concentrating according to the usual methods.

The silyl enol ethers usable in the invention are compounds represented by the general formula

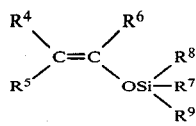

[$R^4$, $R^5$ and $R^6$ are hydrogen or a straight-chain or branched-chain, saturated or unsaturated aliphatic, cycloaliphatic (alicyclic) or aromatic hydrocarbon group having 1 to 30 carbon atoms (which may contain N, O, P or S), and $R^4$ and $R^5$ or $R^4$ and $R^6$ may be combined to form a ring. $R^7$, $R^8$ and $R^9$ are a straight-chain or branched-chain, saturated or unsaturated aliphatic, cycloaliphatic (alicyclic) or aromatic hydrocarbon group having 1 to 20 carbon atoms.]. The following are examples,

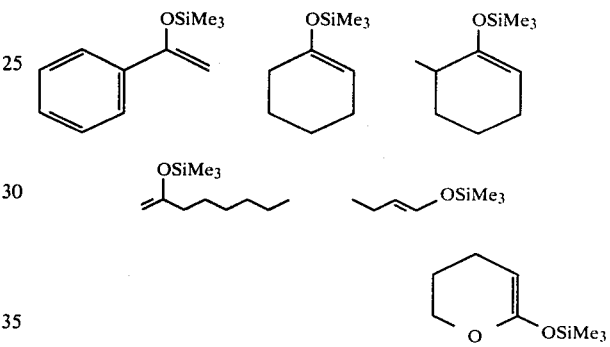

and the like (where, Me indicates methyl).

These compounds can be prepared by a method proposed, for example, by Stork et al (J. Am. Chem. Soc., Vol. 90, p. 4462–4464 (1968).

Among the reagents usable in the invention, organoaluminum compounds represented by the general formula $RnAlX_{3-n}$ (R indicates an alkyl group having 1 to 20 carbon atoms. X indicates hydrogen or halogen n is a real number limited by $0 \leq n \leq 3$.) can be used particularly advantageously.

As examples, trimethylaluminum, triethylaluminum, tripropylaluminum, tributylaluminum, trihexylaluminum, trioctylaluminum, tridecylaluminum, dimethylaluminum chloride, diethylaluminum chloride, dipropylaluminum chloride, dibutylaluminum chloride, propylaluminum dichloride, butylaluminum sesquichloride, propylaluminum sesquichloride, diethylaluminum hydride, diethylaluminum hydride, dibutylaluminum hydride, dithylaluminum bromide, aluminum chloride and the like can be mentioned.

Preferable compounds are dialkylaluminum halides such as diethylaluminum chloride, etc., alkylaluminum dihalides such as ethylaluminum dichloride, etc., alkylaluminum sesquihalides such as ethylaluminum sesquichloride, etc., and their mixtures.

Although other Lewis acids ($SnCl_4$, $FeCl_3$, $TiCl_4$, etc.) can also be used as the reagents, but they are not as advantageous from the standpoint of yield of β-acylenamine. The mixing ration of oxime sulfonate, silyl enol ether and reagent is not confined particularly, but a molar ratio of 1:0.1:0.1 to 1:5:20 is selected preferably.

The condensation reaction is carried out preferably in such solvents as coordinate or react with the organometal compounds and have no harmful influence on the reaction between oxime sulfonate and silyl enol ether (hereinafter referred to as inactive solvents) under the consideration of the handling of reagent. As said inactive solvents, for example, aliphatic hydrocarbons such as pentane, hexane, heptane, etc., alicyclic hydrocarbons such as cyclohexane, etc., aromatic hydrocarbons such as benzene, toluene, xylene, etc. and halogenated hydrocarbons such as dichloromethane, trichloromethane, butyl chloride, monochlorobenzene, etc. can be mentioned. The concentration of reagent in the inert solvent is arbitrary.

There is no particular restriction in the condensation reaction, but the reaction is carried out by mixing oxime sulfonate, silyl enol ether and reagent at $-100°$ to $30°$ C., preferably at $-80°$ to $0°$ C. and stirring for several minutes to scores of hours.

At a temperature of lower than $-100°$ C. or higher than $30°$ C., the intended $\beta$-acylenamine is sometimes not, obtained because of the change of the reactivity of the reagent. An order of addition of oxime sulfonate, silyl enol ether and reagent is arbitrary, provided the reagent is not added at the end. In the following, the invention is illustrated using examples, but the invention is not limited by the following examples.

EXAMPLE 1-13

To a mixture of oxime mesylate (1 mmol) and silyl enol ether (1.1 mmol) in 3 ml of anhydrous dichloromethane, 3 ml of hexane solution in which is dissolved diethylaluminum chloride (3 mmol) or 2 ml of toluene solution in which is dissolved ethylaluminum dichloride (2 mmol) is added at $-78°$ C. under an atmosphere of argon. After 30 min., the temperature is raised to room temperature and the stirring is continued further for 30 min. After determining the progress of the reaction by means of TLC, the product was treated with 5% sodium hydroxide solution, extracted with dichloromethane and purified by means of column chromatography to obtain the intended $\beta$-acylenamine as a solid to liquid state.

These results are shown in Table 1.

The calculated values and the observed ones of the products in Example 3, 4, 6, 8 and 12 determined by elementary analysis are shown in Table 2.

In addition, the infrared spectra of the products in Example 1, 3, 4, 5, 6, 8, 11 and 12 are given in the attached table respectively.

Furthermore, the nuclear magnetic resonance spectra of products in Example 1, 4, 5, 6, 8, 10 and 12 are also given in the attached table, respectively.

TABLE 1

| Example No. | Silyl enol ether | Oxime mesylate $R^1$ | $R^2$ | Reaction agent | Product | Yield (%) |
|---|---|---|---|---|---|---|
| 1 | OSiMe₃ (1-phenylvinyl) | —(CH₂)₅— | | Et₂AlCl | (phenyl ketone with HN-cycloheptyl enamine) | 58 |
| 2 | | | | EtAlCl₂ | | 58 |
| 3 | Same as above | Me | Me | Et₂AlCl | (phenyl ketone with O HNMe enamine) | 65 |
| 4 | OSiMe₃ (cyclohexenyl) | Me | Me | EtAlCl₂ | (cyclohexanone with HNMe enamine) | 69 |
| 5 | OSiMe₃ (methylcyclohexenyl) | —(CH₂)₅— | | EtAlCl₂ | (methylcyclohexanone with HN-cycloheptyl enamine) | 82 |
| 6 | OSiMe₃ (alkyl enol ether) | Et | Et | Et₂AlCl | (alkyl ketone with HN enamine) | 95 |
| 7 | | | | EtAlCl₂ | | 67 |

TABLE 1-continued

| Example No. | Silyl enol ether | Oxime mesylate R¹ | R² | Reaction agent | Product | Yield (%) |
|---|---|---|---|---|---|---|
| 8 | Same as above | —CHCH₃(CH₂)₄— | | Et₂AlCl | | 90 |
| 9 | | | | EtAlCl₂ | | 86 |
| 10 | ⟋⟍⟋OSiMe₃ | —(CH₂)₅— | | EtAlCl₂ | | 53 |
| 11 | 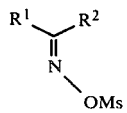 | Me | Me | Et₂AlCl | | 48 |
| 12 | | —(CH₂)₁₁— | | Et₂AlCl | | 88 |
| 13 | ⟋⟍⟋OSiMe₃ | —(CH₂)₁₁— | | Et₂AlCl | 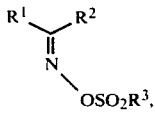 | 54 | where, R¹ and R² in oxime mesylate indicate the substituents in the following formula.

$$\underset{\underset{\text{OMs}}{\overset{\|}{N}}}{R^1\diagdown\diagup R^2}$$

Besides, TLC means thin layer chromatography.

TABLE 2

| Example No. | Element analyzed | Calculated value | Observed value |
|---|---|---|---|
| 3 | C | 75.40 | 75.43 |
| | H | 7.48 | 7.40 |
| | N | 7.99 | 7.95 |
| 4 | C | 70.55 | 71.00 |
| | H | 9.87 | 9.96 |
| 6 | C | 73.88 | 74.38 |
| | H | 11.92 | 12.15 |
| 8 | C | 75.90 | 76.17 |
| | H | 11.46 | 11.75 |
| 12 | C | 80.22 | 80.36 |
| | H | 9.76 | 9.77 |
| | N | 4.68 | 4.58 |

Brief Description of the Drawing

FIG. 1 to FIG. 8 are drawings which indicate the analytical results of products in Examples 1, 3, 4, 5, 6, 8, 11 and 12 of the invention by the use of an infrared spectrophtometer.

Figure 1:
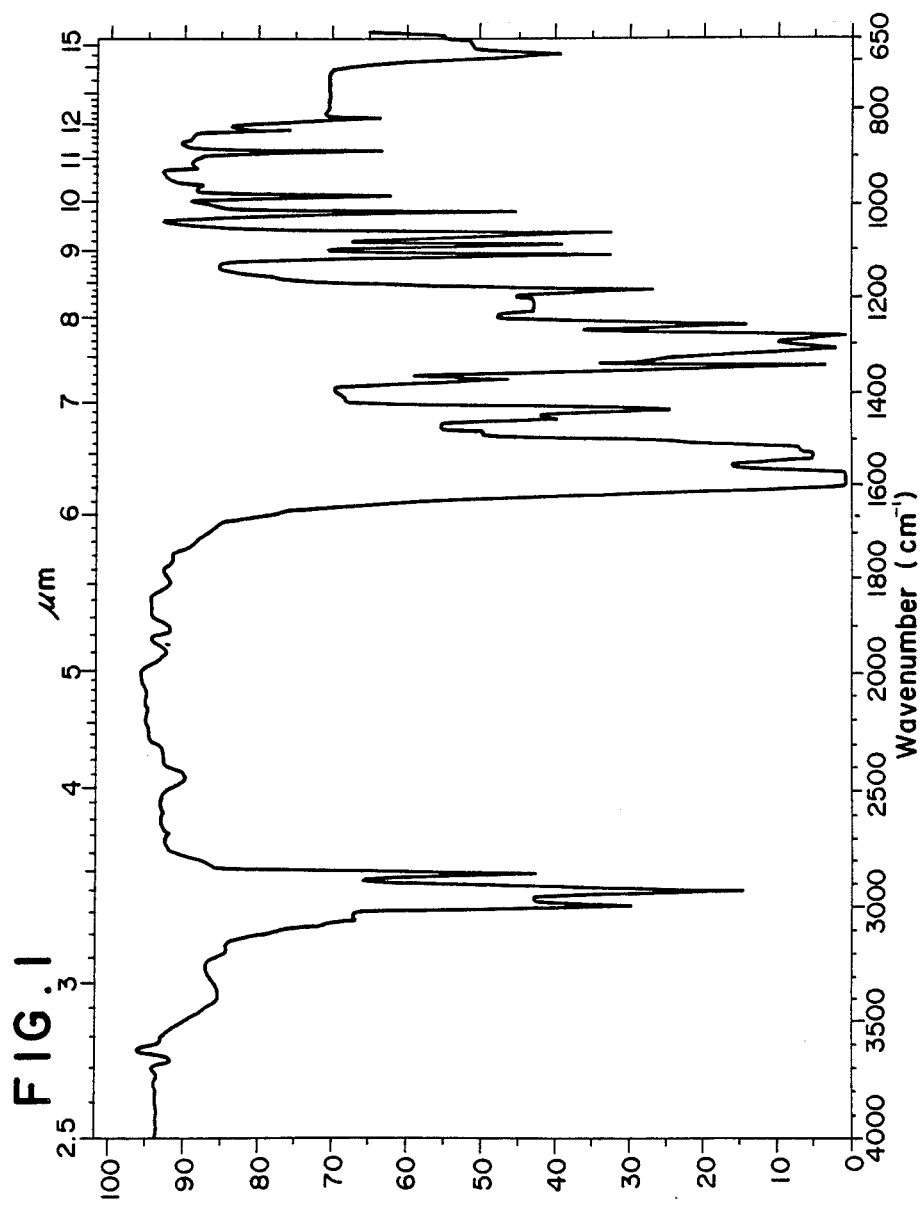
Figure 2:
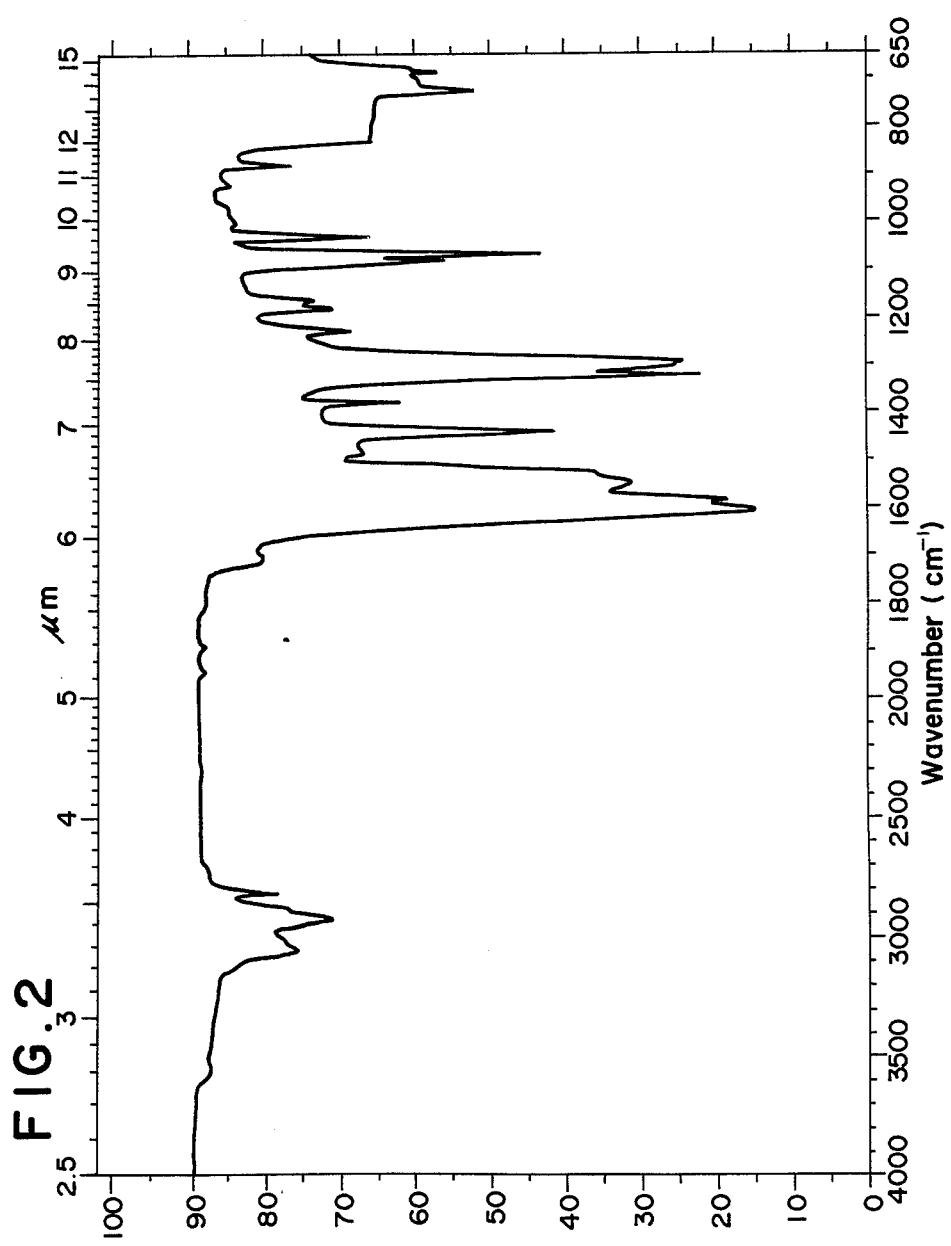
Figure 3:
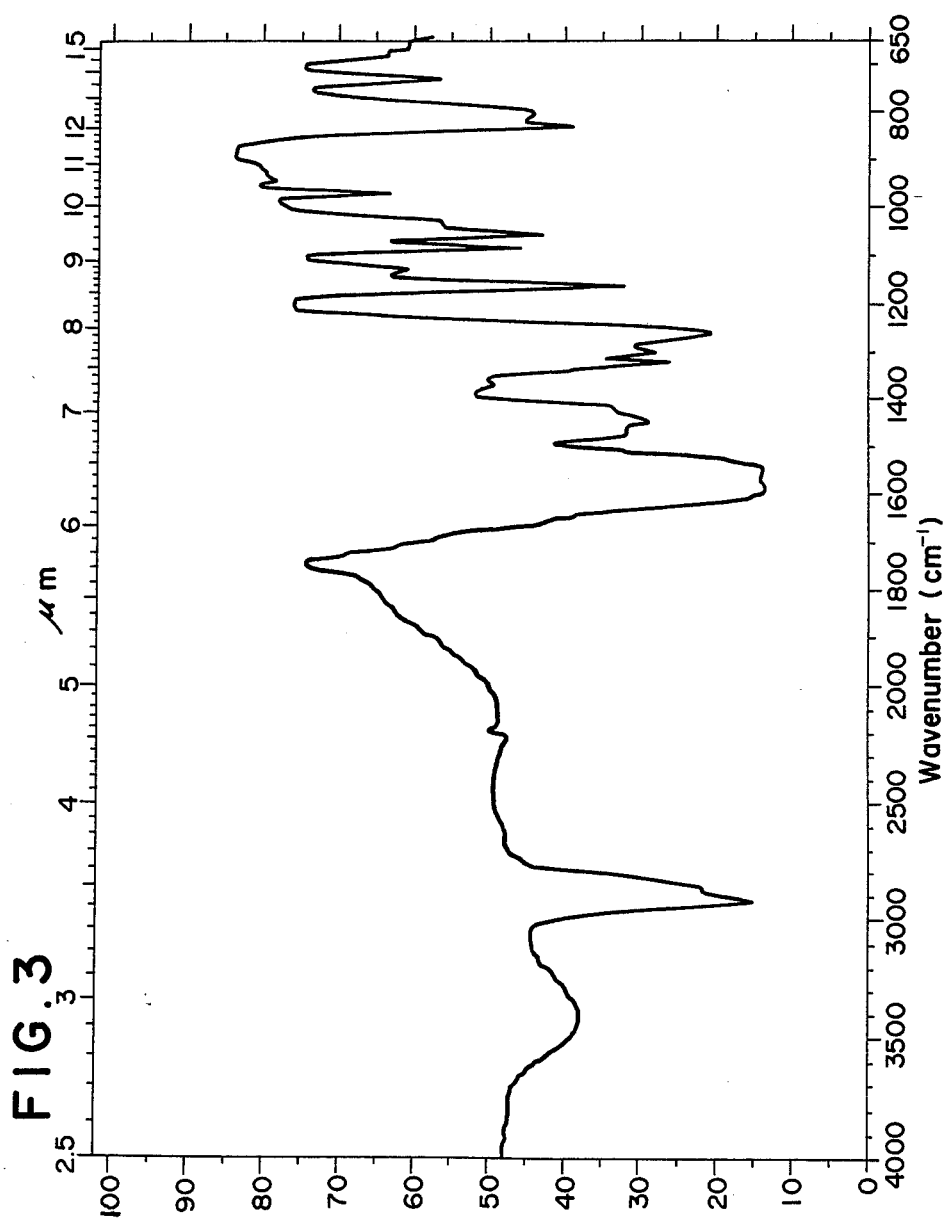
Figure 6:
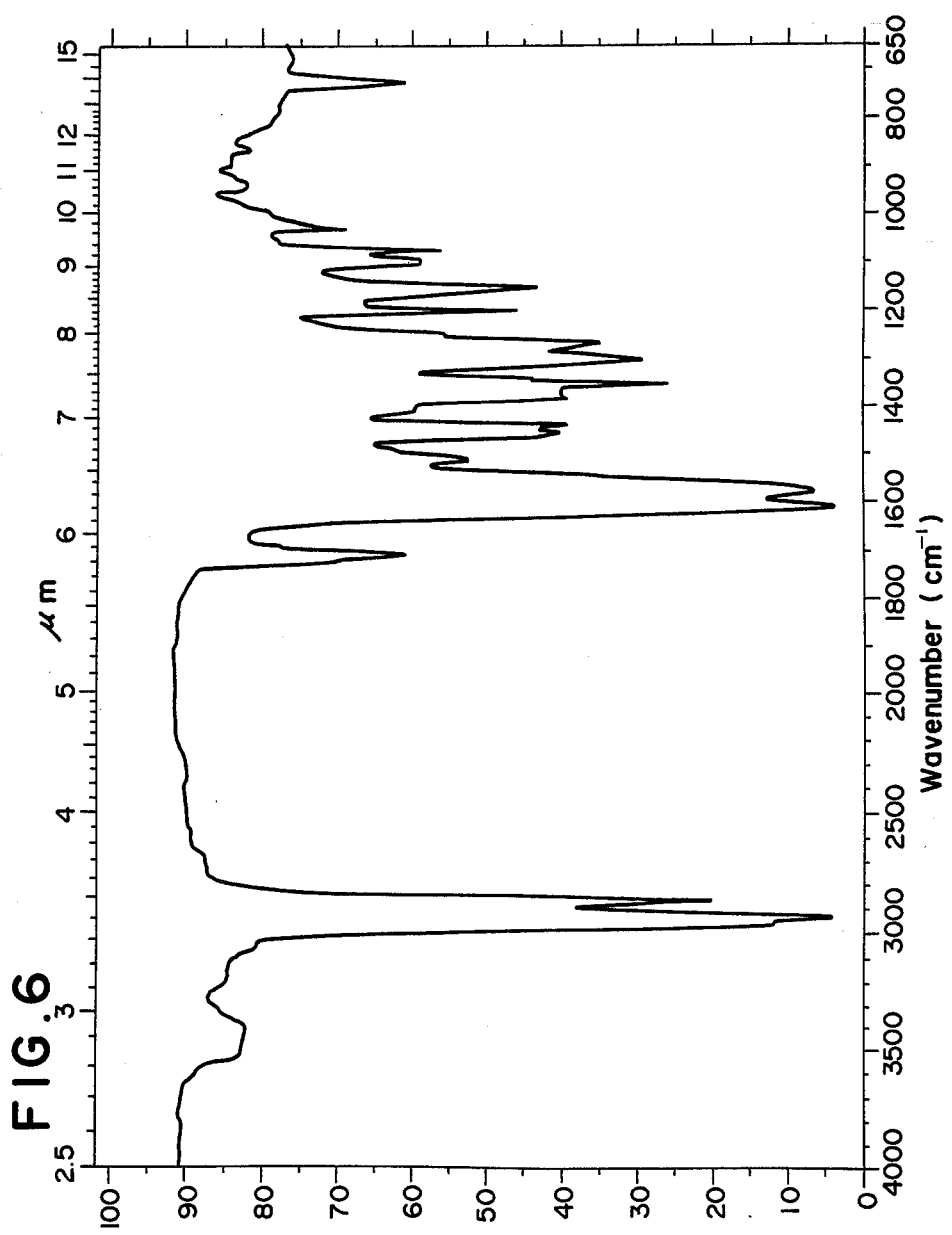
Figure 7:
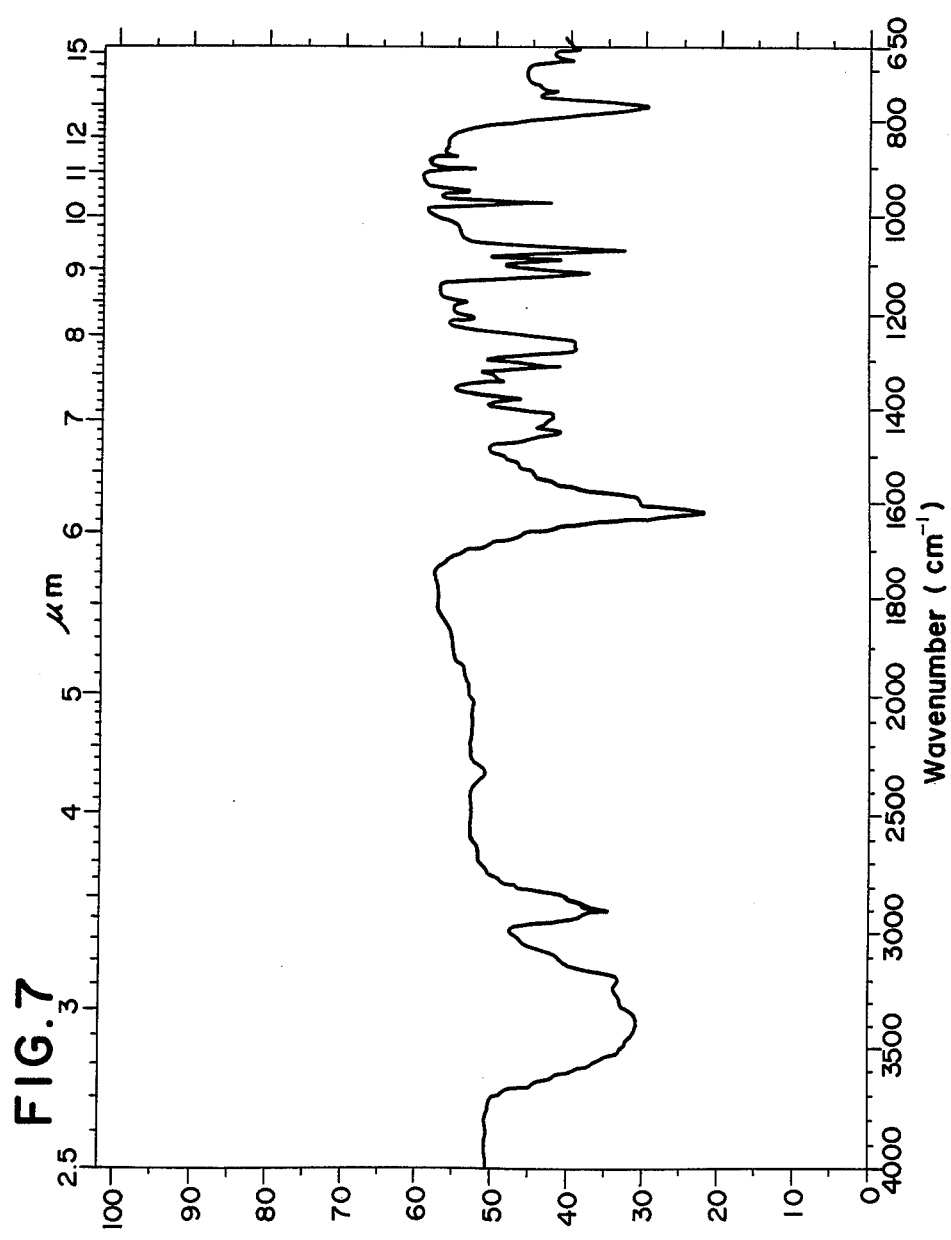
Figure 8:
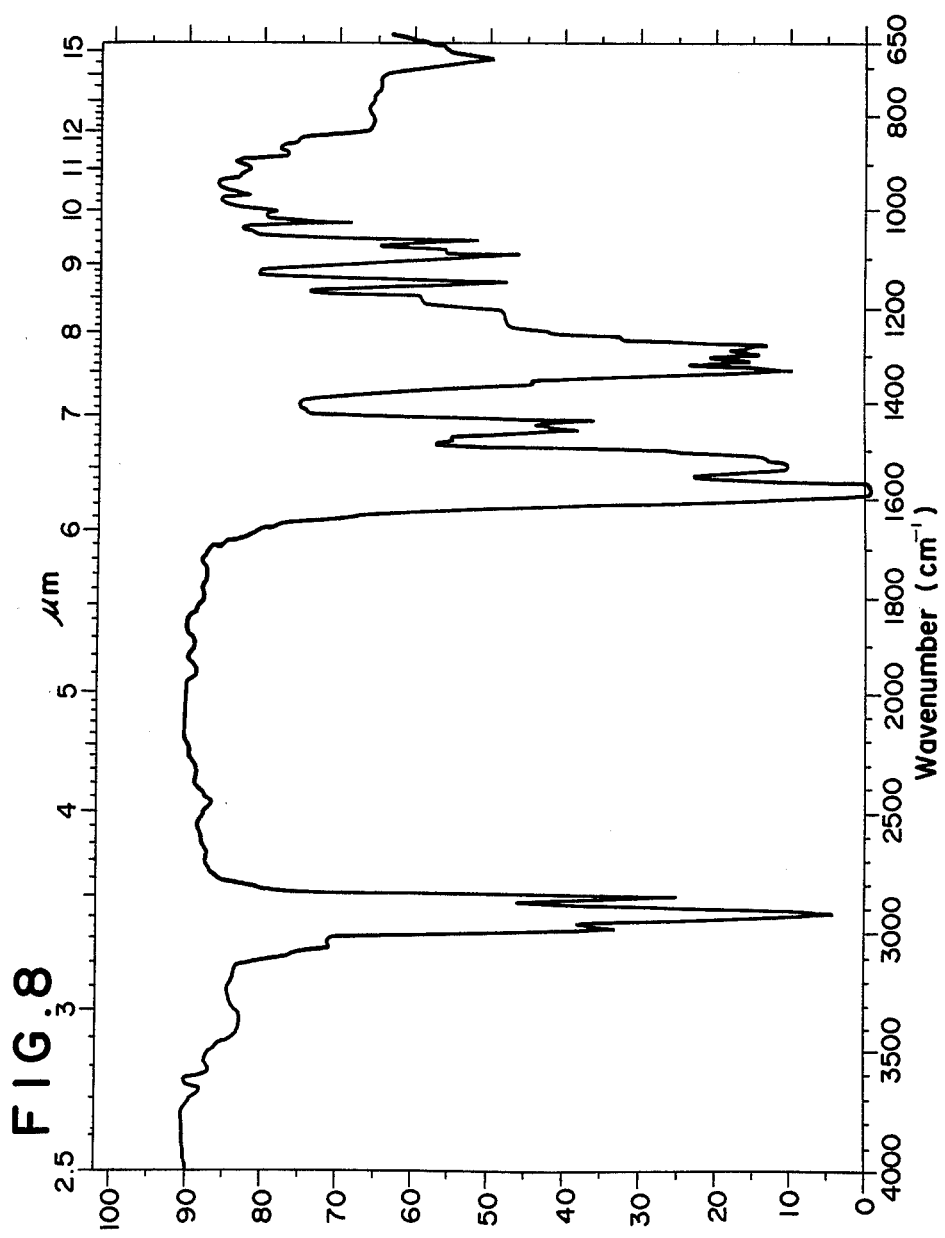
Figure 9:
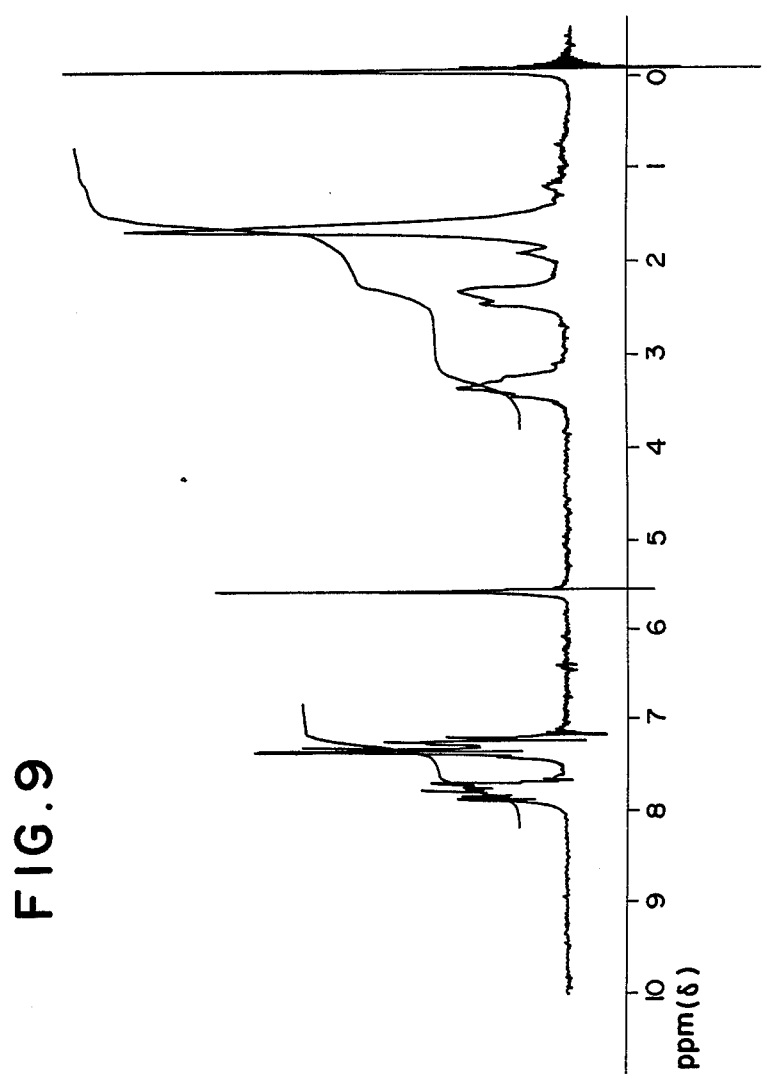
FIG. 9 to FIG. 15 are drawings which indicate the analytical results of the products in Examples 1, 4, 5, 6, 8, 10 and 12 of the invention by the use of nuclear magnetic resonance (NMR).
Figure 10:
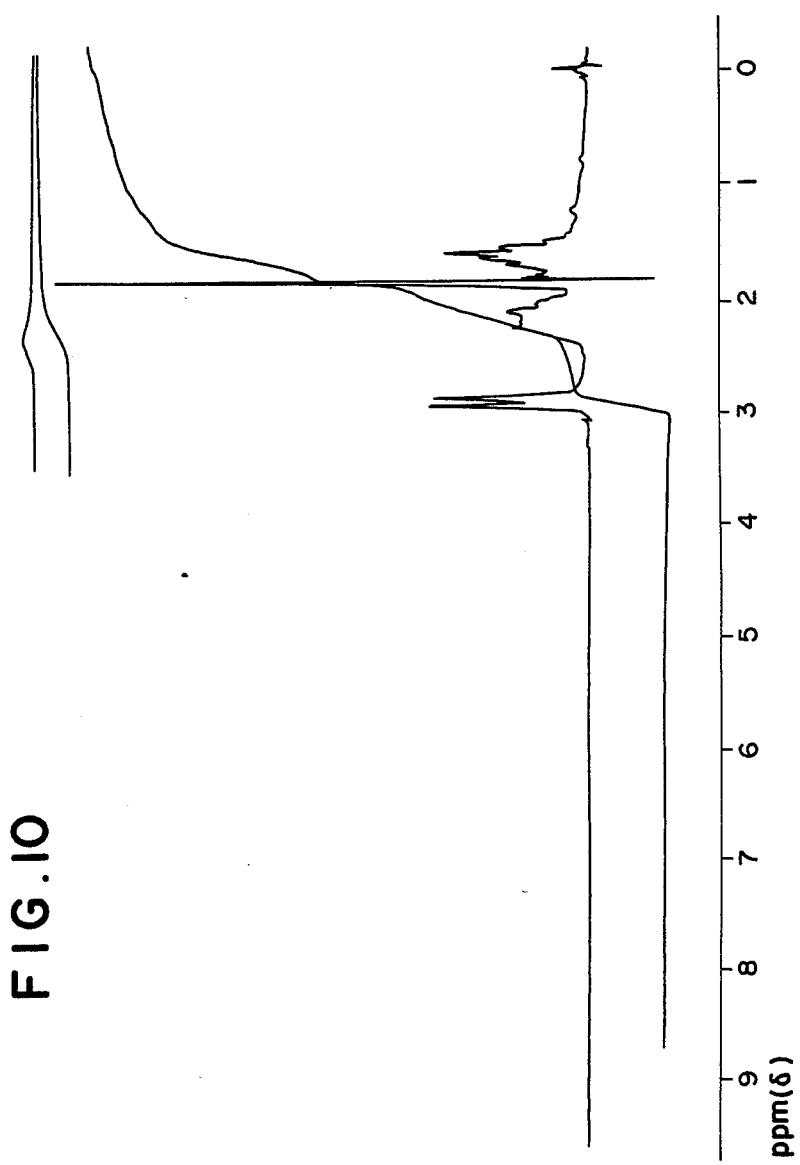
Figure 11:
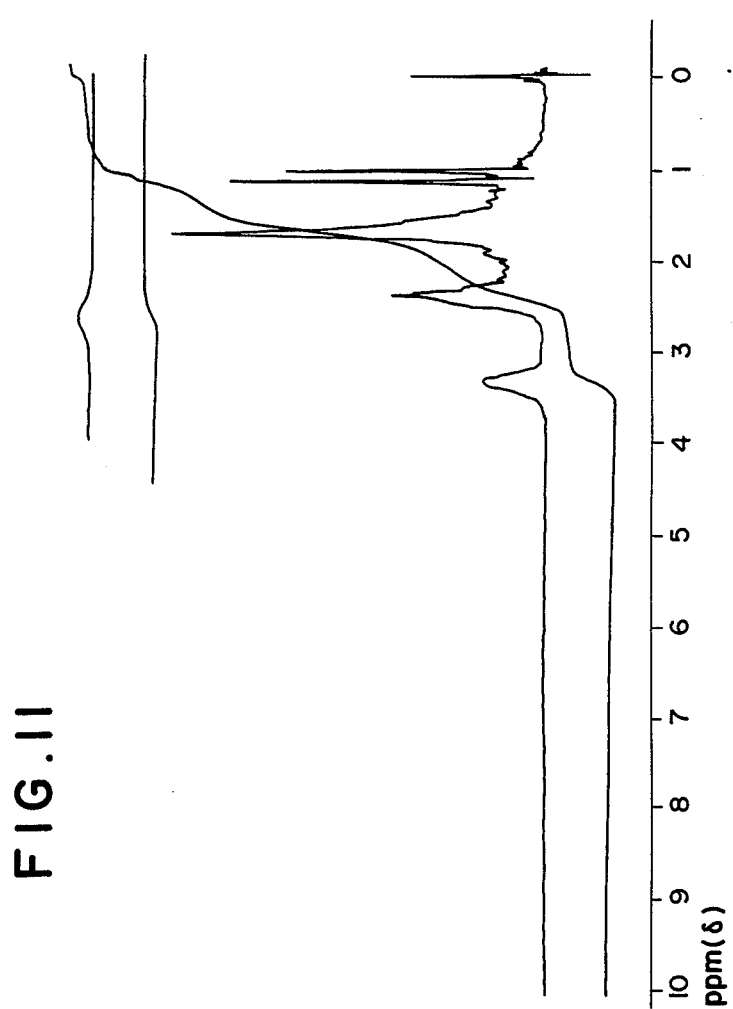
Figure 12:
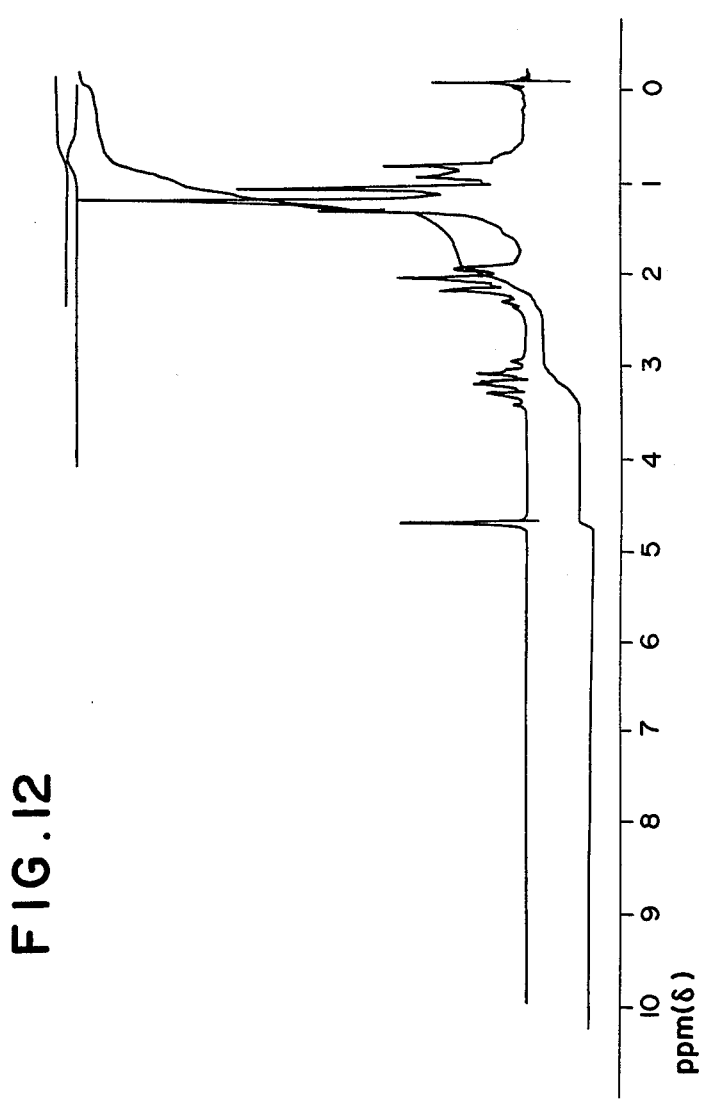
Figure 13:
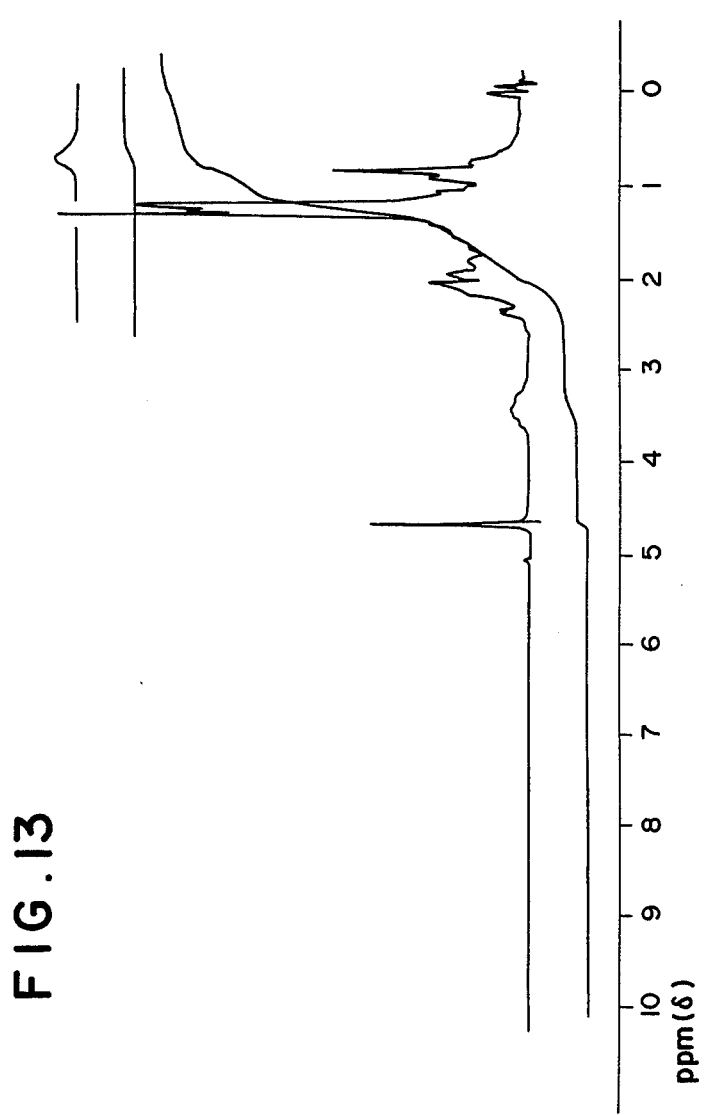
Figure 14:
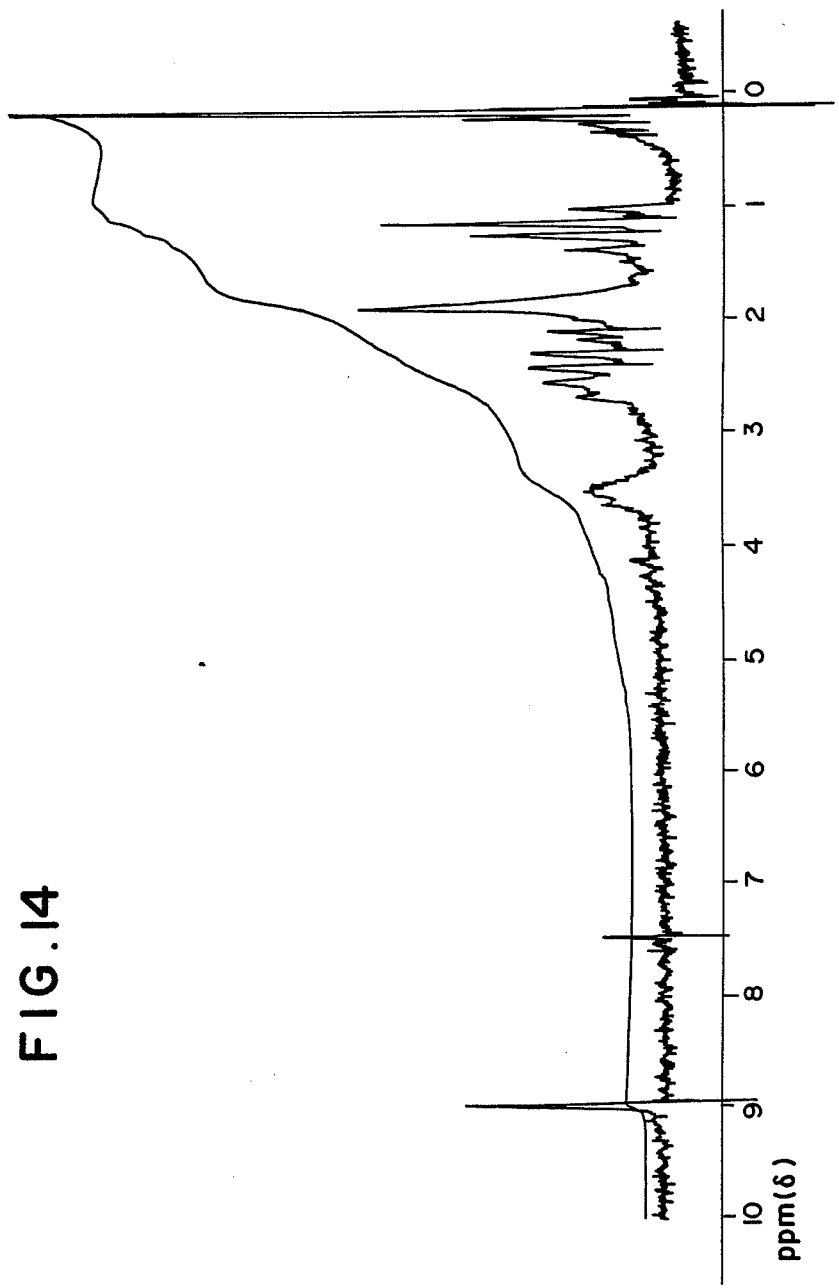
Figure 15:
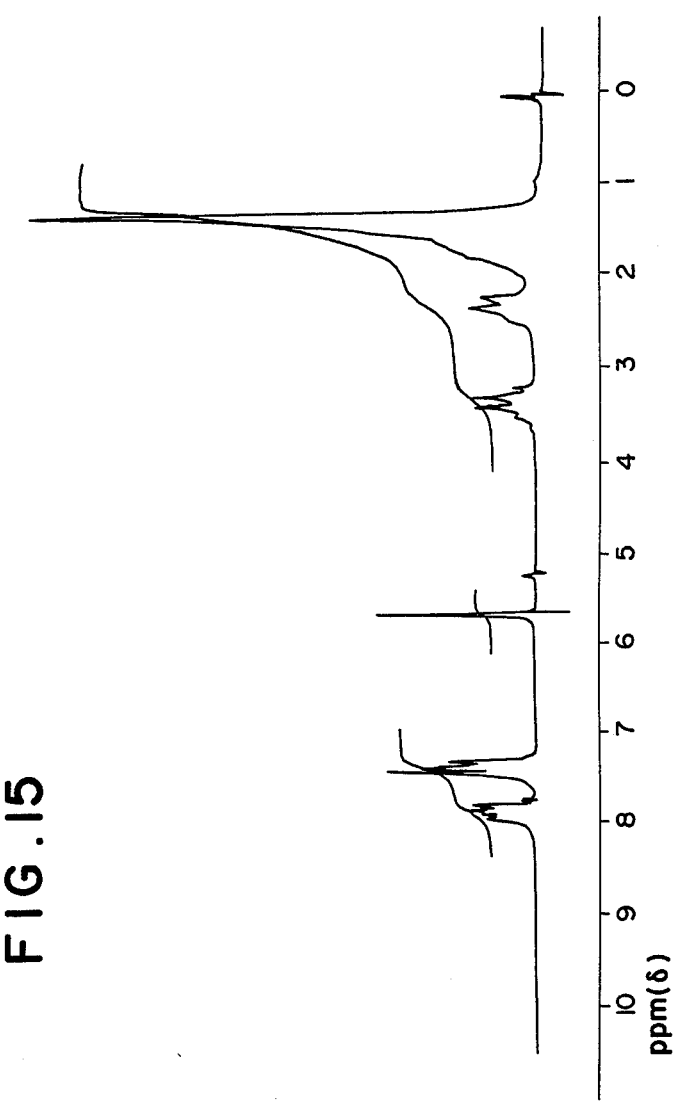

What is claimed is:

1. A method of making a β-acylenamine comprising condensing an oxime sulfonate with a silyl enol ether in the presence of a reagent.

2. A method of making a β-acylenamine described in claim 1, the oxime sulfonate thereof being represented by the following formula, $$\underset{\underset{\text{OSO}_2\text{R}^3}{\overset{\|}{N}}}{R^1\diagdown\diagup R^2},$$

wherein R¹ and R², which can be the same or different, are hydrogen or a straight-chain or branched-chain, saturated or unsaturated aliphatic, cycloaliphatic or aromatic hydrocarbon group having 1 to 30 carbon atoms and which can contain N, O, P or S, and which can be combined to form a ring, R³ is a straight-chain or branched-chain, saturated or unsaturated aliphatic, cycloaliphatic or aromatic hydrocarbon group having 1 to 20 carbon atoms.

3. A method of making a β-acylenamine described in claim 1, the silyl enol ether thereof being represented by the following formula,

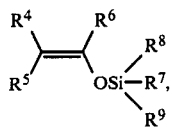

wherein, $R^4$, $R^5$ and $R^6$ are the same or different and are hydrogen or a straight-chain or branched-chain, saturated or unsaturated aliphatic, cycloaliphatic or aromatic hydrocarbon group having 1 to 30 carbon atoms and, which can contain N, O, P or S, and $R^4$ and $R^5$ or $R^4$ and $R^6$ can be combined to form a ring, and wherein $R^7$, $R^8$ and $R^9$ are the same or different and are alkyl having 1 to 20 carbon atoms.

4. A method of making a β-acylenamine described in claim 1, the reagent thereof being a compound of a metal belonging to a or b of the first to the fourth group, a of the fifth to the seventh group, or the eighth group in the periodic table.

5. A method of making a β-acylenamine described in claim 1, the reagent thereof being a compound of aluminum.

6. A method of making a β-acylenamine described in claim 1, the reagent thereof being represented by the formula, $$R_nAlX_{3-n},$$

wherein R is alkyl of 1 to 20 carbon atoms X is hydrogen, halogen, —OR″, where R″ is alkyl of 1 to 20 carbon atoms, —CN, or

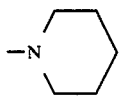

which can be substituted at the 2- or 6- position and n is a real number limited by $0 \leq n \leq 3$.

* * * * *